(12) United States Patent
Hegde et al.

(10) Patent No.: US 8,653,306 B1
(45) Date of Patent: Feb. 18, 2014

(54) PROCESS FOR PRODUCTION OF SERINOL AND ITS BIS-ADDUCT

(71) Applicant: Penn A Kem LLC, Memphis, TN (US)

(72) Inventors: Shridhar G. Hegde, Germantown, TN (US); Lei Zhao, Cordova, TN (US)

(73) Assignee: Penn A Kem LLC, Memphis, TN (US)

( * ) Notice: Subject to any disclaimer, the term of this patent is extended or adjusted under 35 U.S.C. 154(b) by 0 days.

(21) Appl. No.: 13/694,664

(22) Filed: Dec. 21, 2012

Related U.S. Application Data

(60) Provisional application No. 61/631,143, filed on Dec. 28, 2011.

(51) Int. Cl.
*C07C 209/26* (2006.01)
(52) U.S. Cl.
USPC ........................................................ 564/472
(58) Field of Classification Search
USPC ........................................................ 564/472
See application file for complete search history.

(56) References Cited

U.S. PATENT DOCUMENTS

| | | | | |
|---|---|---|---|---|
| 4,221,740 A | * | 9/1980 | Pfeiffer | 564/495 |
| 4,448,999 A | * | 5/1984 | Thewalt et al. | 564/495 |
| 4,503,252 A | | 3/1985 | Felder et al. | |
| 5,023,379 A | | 6/1991 | Felder et al. | |
| 5,998,669 A | * | 12/1999 | Klix et al. | 564/472 |
| 6,916,948 B2 | | 7/2005 | Fleet et al. | |

FOREIGN PATENT DOCUMENTS

| | | |
|---|---|---|
| WO | WO9527695 | 10/1995 |
| WO | WO0158848 | 8/2001 |

OTHER PUBLICATIONS

Scott, David A. "Synthesis of bis(1,3-Dihydroxy-isopropyl)amine by Reductive Amination of Dihydroxyacetone . . .", Tetrahedron Letters 40 (1999) 7581-7584. Elsevier Science Ltd.

* cited by examiner

*Primary Examiner* — Brian J Davis
(74) *Attorney, Agent, or Firm* — Grace L. Bonner

(57) ABSTRACT

An improved method for the production of 2-amino-1,3-propanediol (serinol) and its bis-adduct, 2,2'-iminobis-1,3-propanediol, from dihydroxyacetone and ammonia in the presence of a hydrogenation catalyst such as Raney nickel, followed by separation using an acidic ion-exchange resin.

18 Claims, No Drawings

PROCESS FOR PRODUCTION OF SERINOL AND ITS BIS-ADDUCT

CROSS REFERENCE TO RELATED APPLICATIONS

None.

NAMES OF PARTIES TO A JOINT RESEARCH AGREEMENT

None.

SEQUENCE LISTING

None.

BACKGROUND OF THE INVENTION

Serinol (2-amino-1,3-propanediol) is used as an intermediate to make many different fine chemicals, including pharmaceuticals. Examples are iopamidol (U.S. Pat. Nos. 4,001,323, 4,348,377, and 5,035,877); voglibose (European Patent EP 0260121); and dilmapimod (U.S. Publ. 2006/258687). Methods for its manufacture include the catalytic hydrogenation of 1,3-dihydroxyacetone oxime (U.S. Pat. No. 5,922,917); the reaction of nitromethane and formaldehyde (EP 0436414); and the reaction of dihydroxyacetone with hydrazine (CZ 289303).

Another process (U.S. Pat. No. 5,023,379) is a two-step method wherein dihydroxyacetone is mixed with methanol at low temperatures, after which aqueous ammonia is added. Later, Raney nickel is added and hydrogen is introduced under pressure. The reaction mixture is filtered to remove the catalyst, water is removed under vacuum, and serinol is recovered by conversion into the oxalate with oxalic acid dihydrate.

In another synthetic route, 2-nitro-1,3-propanediol sodium salt is hydrogenated in the presence of heavy metal catalysts to produce serinol in high yields, but with the disadvantage of the cost of the catalyst (U.S. Pat. No. 6,509,504). Yet another route uses the expensive starting material, 2-chloro-2-nitro-1,3-propanediol (U.S. Pat. No. 5,053,545).

Another process is the reductive amination of dihydroxyacetone. It has the advantage of producing serinol using inexpensive reactants with a relatively inexpensive catalyst, Raney nickel, but produces byproducts which can be expensive to remove from the serinol (see, for example, WO 9527695). Other, more expensive, catalysts may also be used (JP6009512).

The bis-adduct of serinol, 2,2'-iminobis-1,3-propanediol, is also useful, but generally as an intermediate to produce polymers, including dendrimers (U.S. Pat. No. 6,916,948). It has been produced by the reductive amination of dihydroxyacetone dimer using sodium cyanoborohydride and ammonium chloride in methanol and acetic acid. The product was purified by dissolving the residue in water and introducing the solution to an acidic ion-exchange resin and eluting with water and then aqueous ammonia.

However, the known methods to produce serinol or its bis-adduct are less than desirable due to the cost or toxicity of the reactants or by-products. The present invention provides for the production of either compound, using the same reactants, but varying the process parameters. Surprisingly, the two compounds can be easily separated from each other, resulting in a reduced cost to produce either compound.

SUMMARY OF THE INVENTION

The present invention is an improved process for the reductive amination of dihydroxyacetone so as to selectively produce 2-amino-1,3-propanediol (serinol) or 2,2'-iminobis-1,3-propanediol (the bis-adduct of serinol). The reaction is controlled to produce more of one or the other by reversing the stoichiometry of the reactants, and the two products are readily separated using an acidic ion-exchange resin. Thus, it has been found that the use of ammonia in stoichiometric excess relative to dihydroxyacetone produces more serinol than its bis-adduct (Process 1), but the use of dihydroxyacetone in stoichiometric excess to ammonia produces more 2,2'-iminobis-1,3-propanediol (Process 2).

A hydrogenation catalyst is used, preferably Raney nickel. Raney nickel can be either un-promoted or promoted with a transition metal. A preferred promoter is molybdenum. Powdered elemental nickel or nickel supported on gamma-aluminum may also be used as the catalyst in the present invention, but with less desirable results. Raney cobalt, ruthenium on carbon support, rhodium on carbon support, and palladium on carbon support will work as well as Raney nickel; however, these catalysts are very expensive compared to nickel.

Hydrogen is introduced under pressure, and the reactants are heated. The hydrogen is preferably between 20 and 1500 psi, more preferably between 150 and 300 psi, and most preferably around 250 psi. The temperature is preferably between 0 and 150° C., more preferably between 45 and 90° C., and most preferably around 65° C.

Surprisingly, the amine products of either set of reaction conditions can be separated from each other using an acidic ion-exchange resin. The products of Process 1 are introduced into the resin, which is preferably packed in a column, and eluted first with methanol to remove byproducts, including, surprisingly, the small amount of the bis-adduct produced, followed by aqueous ammonia to recover serinol. The products of Process 2 are purified in the same manner. The mixture is introduced into the resin, which is preferably packed in a column, but eluted with methanol to recover 2,2'-iminobis-1,3-propanediol.

An alternate method for making 2,2'-iminobis-1,3-propanediol is by the hydrogenation of a mixture of serinol and dihydroxyacetone. The same conditions of the other processes may be used, and Raney nickel is the preferred hydrogenation catalyst.

Advantageously, the small amount of 2,2'-iminobis-1,3-propanediol produced in Process 1 can be recovered from the methanol wash of the ion-exchange resin and used. More advantageously, the small amount of 2-amino-1,3-propanediol produced in Process 2 can be recovered from the ion-exchange resin following the removal of the 2,2-iminobis-1,3-propanediol by washing the loaded resin with aqueous ammonia, thus making the process for making the bis-adduct more cost effective by recovering a valuable byproduct, serinol.

DETAILED DESCRIPTION OF THE INVENTION

Process 1 and Process 2 use the same reactants; however, the stoichiometry differs between the two. In Process 1 ammonia, in aqueous or gaseous form, is used in excess to dihydroxyacetone, with a minimum ratio of about 4:1, preferably about 10:1, and up to 100:1. The order of the addition of the reactants is not crucial, only the stoichiometry.

Process 2 uses the opposite stoichiometry of reactants. In this case, dihydroxyacetone is in excess to ammonia. As in Process 1, aqueous or gaseous ammonia is added to dihydroxyacetone in the presence of the catalyst and under hydrogen pressure. Dihydroxyacetone is in excess of ammonia. Any ratio above 1:1 will work. A ratio of between 1.5:1 and 2:1 is preferred. The order of the addition of the reactants is not crucial, but for Process 2 the addition of ammonia to dihydroxyacetone is preferred.

Dihydroxyacetone and ammonia are readily available. Dihydroxyacetone suppliers include Merck EMD Chemicals, ARD-Soliance, Sigma-Aldrich, MP Biomedicals, and Acros Organics. There is no specific requirement in terms of purity. Ammonia gas and ammonium hydroxide are available from Avantor Performance Materials, Air Products & Chemicals, Fisher Scientific Chemicals, and Dyno Nobel Inc. Ammonia gas needs to be typically >99% purity. Ammonium hydroxide solution in water can be of various strengths, but typically at least 28%.

The optimum amount of hydrogenation catalyst as described above can be readily determined by one of skill in the art. The preferred type of catalyst is unpromoted Raney nickel, for example, A5000 Nickel catalyst from Johnson Matthey, or molybdenum-promoted nickel, for example, A7000 Nickel catalyst from Johnson Matthey.

The process of the present invention, in either stoichiometric ratio, could be carried out as a continuous process, metering in a mixture of reactants at the desired stoichiometry. The same catalysts can be used, and the optimum reaction time and temperatures for a continuous process can be readily determined by one of ordinary skill in the art.

The ion-exchange resin used in the purification of the desired product from the reaction of the present invention is preferably strongly acidic. Such resins can be obtained from a number of suppliers. An example is Amberlyst® 15 from Dow Chemical Company. The resin may be used as a slurry which is then filtered or, more preferably, packed in a column.

Another method for making 2,2'-iminobis-1,3-propanediol (the bis-adduct of serinol) is by first obtaining serinol by any method, the one of the present invention (Process 1) being preferred. A mixture of serinol and dihydroxyacetone is hydrogenated using the same general conditions as for Process 1 and Process 2 to produce the bis-adduct. It is isolated from the reaction mixture as described herein for Process 2.

The process of the present invention is illustrated by the following examples. A typical procedure is to introduce a solution of 1,3-dihydroxyactone in water to a mixture of the hydrogenation catalyst and ammonium hydroxide or ammonia in methanol that is being agitated in an autoclave at a specified temperature and at a specified pressure of hydrogen atmosphere. After the expiration of the predetermined reaction time, the autoclave is cooled and depressurized. The product is then purified by the use of ion-exchange resin and recrystallization as illustrated in the examples. Product analysis is typically performed with gas chromatography (GC) under the following set of conditions: Column Length, 30 Meters; Column Type, Carbowax; Thermal Conductivity Detector (TCD); Gas Flow Rate, 11 ml/min.; Run Time, 25 min.; and Temperature Program:
1. Initial Temperature: 140° C. Maintaining for 2 min.
2. Temperature Ramp: 20° C./min.
3. Final Temperature: 215° C.

Example 1

In an autoclave, a mixture of Raney nickel (4 g, wet) and ammonium hydroxide solution (257 g, 28% NH3 in water, 4.2 mol) was heated to 65° C. under 250 psi of hydrogen atmosphere. A solution of 1,3-dihydroxyacetone (38 g, 0.42 mol) in methanol (76 ml) was pumped into the autoclave over a period of 3 h. After the addition was complete, the reaction mixture was maintained at 65° C. and 250 psi hydrogen pressure for additional 3 h. The autoclave was then cooled to ambient temperature and depressurized. The resulting reaction mixture was filtered to remove the catalyst. Ammonia and most of the water were removed by distillation under reduced pressure. GC analysis of the crude product showed a mixture of 91% serinol (2-amino-1,3-propanediol) and 7% bis-adduct (2,2'-iminobis-1,3-propanediol).

An aqueous solution of the crude product mixture was loaded to a column of Amberlyst® 15 and eluted with water until neutral pH. GC analysis of the water eluate showed mainly the bis-adduct and other unidentified impurities. The column was then eluted with 300 ml of 4M ammonium hydroxide solution to recover the serinol. The eluate was then stripped under vacuum to remove ammonia and water. The residue was triturated with a 1:1 mixture of 2-butanol and 2-methyltetrahydrofuran to yield crystalline serinol (27 g, 71% yield). Assay by GC: 97%; Assay by titration: 101%.

Example 2

In an autoclave, ammonia gas (72 g, 4.2 mol) was charged to a suspension of Raney nickel (4 g, wet) in methanol (150 ml) and then heated to 65° C. under 250 psi of hydrogen atmosphere. A solution of 1,3-dihydroxyacetone (58% solution in water, 65 g, 0.42 mol) in methanol (50 ml) was pumped into the autoclave over a period of 3 h. After the addition was complete, the reaction mixture was continued to hydrogenate at 65° C. temperature and 250 psi hydrogen pressure for additional 3 h. The autoclave was then cooled to ambient temperature and depressurized. The reaction mixture was filtered to remove the catalyst, and the filtrate was stripped under reduced pressure to remove ammonia and most of the water. Analysis of the crude productl by GC showed 90% serinol and 8% bis-adduct.

An aqueous solution of the crude product was loaded to a column of Amberlyst® 15 and successively eluted with water and 4 M ammonium hydroxide as described in Example 1. After ammonia and water were removed by evaporation of the ammonium hydroxide eluate in vacuo, the residue was triturated with 1:1 mixture of 2-butanol and 2-methyltetrahydrofuran to yield crystalline serinol (26.7 g, 70% yield). Assay by GC: 99%; Assay by titration: 97%

Example 3

In an autoclave, ammonia gas (13 g, 0.77 mol) was charged to a suspension of Raney nickel (4 g, wet) in methanol (100 ml) and then heated to 65° C. under 250 psi of hydrogen atmosphere. A solution of 1,3-dihydroxyacetone (58% solution in water, 200 g, 1.29 mol) was pumped into the autoclave over a period of 2 h. After the addition was complete, the reaction mixture was continued to hydrogenate at 65° C. temperature and 250 psi hydrogen pressure for an additional 3 h. The autoclave was cooled to ambient temperature and depressurized. The reaction mixture was filtered to remove the catalyst and evaporated under vacuum to remove ammonia and most of the water. The crude product was shown to contain 2.4% serinol and 90% 2,2'-iminobis-1,3-propanediol by GC analysis.

An aqueous solution of the crude product was loaded to a column of Amberlyst® 15 and eluted with water until neutral pH. GC analysis of the water eluate showed complete removal of serinol (FIG. 5). The water eluate was then evaporated under vacuum, the residue was dissolved in 1:1 mixture of 2-butanol and tetrahydrofuran, treated with activated carbon, and concentrated to yield the bis-adduct 2,2'-iminobis-1,3-propanediol as a viscous oil (65 g, 61%). Assay by GC: 99%

Example 4

In an autoclave, a mixture of serinol (10.6 g, 0.12 mol), 1,3-dihydroxyacetone (10.4 g, 0.12 mol), and Raney nickel (1 g, wet) in methanol (100 ml) was heated to 65° C. under 250 psi hydrogen pressure for 3 h. The autoclave was cooled to ambient temperature and depressurized. The resulting reaction mixture was filtered to remove the catalyst. The filtrate was evaporated under vacuum to remove ammonia and most of the water. The residue was dissolved in a 1:1 mixture of 2-butanol and tetrahydrofuran, treated with activated carbon, and evaporated to give the bis-adduct 2,2'-iminobis-1,3-propanediol as a viscous oil (15 g, 79%). Assay by GC: 99%.

All patents and publications referenced herein are incorporated by reference. The invention has been described in an illustrative manner, and it is to be understood that the terminology which has been used is intended to be in the nature of words of description rather than limitation. Obviously, many modifications and variations of the present invention are possible in light of the above teachings. It is, therefore, to be understood that within the scope of the appended claims, the invention may be practiced otherwise than as specifically described above.

The invention claimed is:

1. A method for production of 2-amino-1,3-propanediol comprising reacting dihydroxyacetone with ammonia under hydrogen pressure and in the presence of a hydrogenation catalyst, wherein the ammonia is in excess to dihydroxyacetone; passing the resulting products through an acidic ion-exchange resin; and releasing 2-amino-1,3-propanediol by washing the resin with aqueous ammonia.

2. The method of claim 1 wherein the temperature of the reaction is maintained between 0 and 150° C.

3. The method of claim 2 wherein the temperature of the reaction is maintained between 45 and 90° C.

4. The method of claim 1 wherein the pressure during the reaction is maintained between 20 and 1500 psi.

5. The method of claim 4 wherein the pressure during the reaction is maintained at approximately 250 psi.

6. The method of claim 1 wherein the ratio of ammonia to dihydroxyacetone is between 4:1 and 100:1.

7. The method of claim 6 wherein the ratio of ammonia to dihydroxyacetone is approximately 10:1.

8. The method of claim 1 wherein the hydrogenation catalyst is Raney nickel.

9. A method for production of 2,2'-iminobis-1,3-propanediol comprising reacting dihydroxyacetone with ammonia under hydrogen pressure and in the presence of a hydrogenation catalyst, wherein the dihydroxyacetone is in excess to ammonia; passing the resulting products through an acidic ion-exchange resin; and releasing 2,2'-iminobis-1,3-propanediol by washing the resin with methanol.

10. The method of claim 9 wherein the temperature of the reaction is maintained between 0 and 150° C.

11. The method of claim 10 wherein the temperature of the reaction is maintained between 45 and 90° C.

12. The method of claim 9 wherein the pressure during the reaction is maintained between 20 and 1500 psi.

13. The method of claim 12 wherein the pressure during the reaction is maintained at approximately 250 psi.

14. The method of claim 9 wherein the ratio of dihydroxyacetone to ammonia is approximately 2:1.

15. The method of claim 9 wherein the hydrogenation catalyst is Raney nickel.

16. The method of claim 9 wherein the acidic ion-exchange resin is further eluted with aqueous ammonia and 2-amino-1,3-propanediol is recovered in addition to 2,2'-iminobis-1,3-propanediol.

17. A method for production of 2,2'-iminobis-1,3-propanediol comprising reacting dihydroxyacetone with 2-amino-1,3-propanediol under hydrogen pressure and in the presence of a hydrogenation catalyst; passing the reaction products through an acidic ion-exchange resin; and releasing 2,2'-iminobis-1,3-propanediol by washing the resin with methanol.

18. The method of claim 17 wherein the hydrogenation catalyst is Raney nickel.

* * * * *